(12) United States Patent
Cao

(10) Patent No.: US 9,700,518 B1
(45) Date of Patent: Jul. 11, 2017

(54) DIP MOLDING PROCESS FOR THE MANUFACTURE OF HARD CAPSULE SHELLS

(71) Applicant: Karl Wei Cao, Richmond (CA)

(72) Inventor: Karl Wei Cao, Richmond (CA)

( * ) Notice: Subject to any disclaimer, the term of this patent is extended or adjusted under 35 U.S.C. 154(b) by 0 days.

(21) Appl. No.: 15/357,693

(22) Filed: Nov. 21, 2016

(51) Int. Cl.
| | |
|---|---|
| *A61K 9/48* | (2006.01) |
| *B29C 41/14* | (2006.01) |
| *B29C 41/46* | (2006.01) |
| *B29C 37/00* | (2006.01) |
| *A61K 9/28* | (2006.01) |
| *B29K 105/00* | (2006.01) |
| *B29L 31/00* | (2006.01) |

(52) U.S. Cl.
CPC ........ *A61K 9/4816* (2013.01); *B29C 37/0025* (2013.01); *B29C 41/14* (2013.01); *B29C 41/46* (2013.01); *B29K 2005/00* (2013.01); *B29K 2105/0032* (2013.01); *B29K 2995/002* (2013.01); *B29K 2995/0056* (2013.01); *B29L 2031/7174* (2013.01)

(58) Field of Classification Search
CPC ........ A61K 9/4816; A61K 9/28; B29C 41/14; B29C 37/0025; B29C 41/46; B29K 2105/0032; B29K 2005/00; B29K 2995/002; B29K 2995/0056; B29L 2031/7174
See application file for complete search history.

(56) References Cited

U.S. PATENT DOCUMENTS

| | | | |
|---|---|---|---|
| 2,526,683 | A | 10/1950 | Murphy |
| 3,256,279 | A | 6/1966 | Karmas |
| 3,784,390 | A | 1/1974 | Hijiya et al. |
| 4,562,020 | A | 12/1985 | Hijiya et al. |
| 4,623,394 | A | 11/1986 | Nakamura et al. |
| 6,331,205 | B1 | 12/2001 | Paris et al. |
| 6,517,865 | B2 | 2/2003 | Cade et al. |
| 6,635,275 | B1 | 10/2003 | Scott et al. |
| 6,635,279 | B2 | 10/2003 | Kolter et al. |

(Continued)

FOREIGN PATENT DOCUMENTS

| | | |
|---|---|---|
| EP | 1072633 A1 | 1/2001 |
| EP | 1157691 A1 | 11/2001 |

(Continued)

*Primary Examiner* — Blessing M Fubara
(74) *Attorney, Agent, or Firm* — Buskop Law Group P.C.; Wendy Buskop

(57) ABSTRACT

A dip molding process for the manufacture of allergen free hard capsule shells includes forming an allergen free solution, increasing the temperature of the allergen free solution, filtering the heated allergen free solution, vacuuming the filtrate to remove from 98 percent to 99 percent of air bubbles forming a reduced bubble filtrate, cooling the reduced bubble filtrate, dipping molding pins into the cooled filtrate, withdrawing the molding pins from the cooled filtrate, drying the molding pins with the cooled filtrate to form hard capsule shells, and coating the hard capsule shells with a vegetarian polishing agent. The formed vegan and allergen free hard capsules are dimensionally stable with a combination of (i) mechanical strength, (ii) resistance to cracking and (iii) resiliency. The created vegan and allergen free hard capsules have a body and cap that easily engage while producing an oxygen barrier for product.

15 Claims, 10 Drawing Sheets

(56) References Cited

U.S. PATENT DOCUMENTS

| | | |
|---|---|---|
| 6,783,770 B2 | 8/2004 | Angel et al. |
| 6,887,307 B1 | 5/2005 | Scott et al. |
| 7,041,315 B2 | 5/2006 | Scott et al. |
| 7,267,718 B2 | 9/2007 | Scott et al. |
| 7,407,669 B2 | 8/2008 | Leung et al. |
| 2001/0024678 A1 | 9/2001 | Scott et al. |
| 2004/0091557 A1 | 5/2004 | Hamann |

FOREIGN PATENT DOCUMENTS

| | | |
|---|---|---|
| EP | 2663294 B1 | 9/2015 |
| GB | 1374199 A | 11/1974 |
| GB | 1533301 A | 11/1978 |
| GB | 1559644 | 1/1980 |
| JP | 2005137935 A | 6/2005 |
| WO | 0018835 A1 | 4/2000 |
| WO | 02088246 A1 | 11/2002 |
| WO | 2005105051 A1 | 11/2005 |
| WO | 2012095746 A1 | 7/2012 |
| WO | WO 2012/095746 A2 * | 7/2012 |

\* cited by examiner

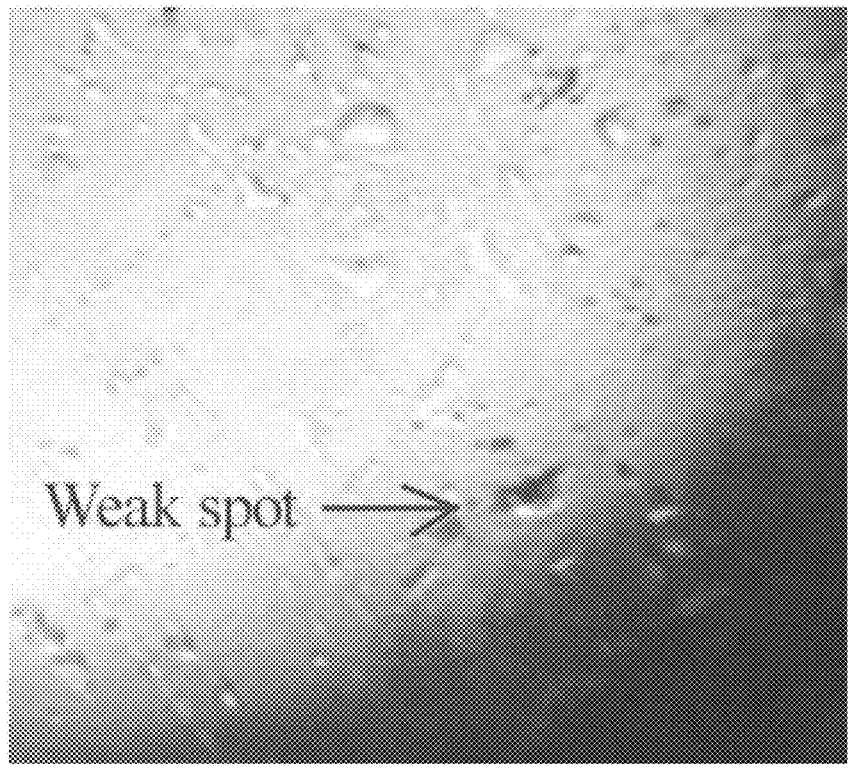
FIGURE 1
FIGURE 2
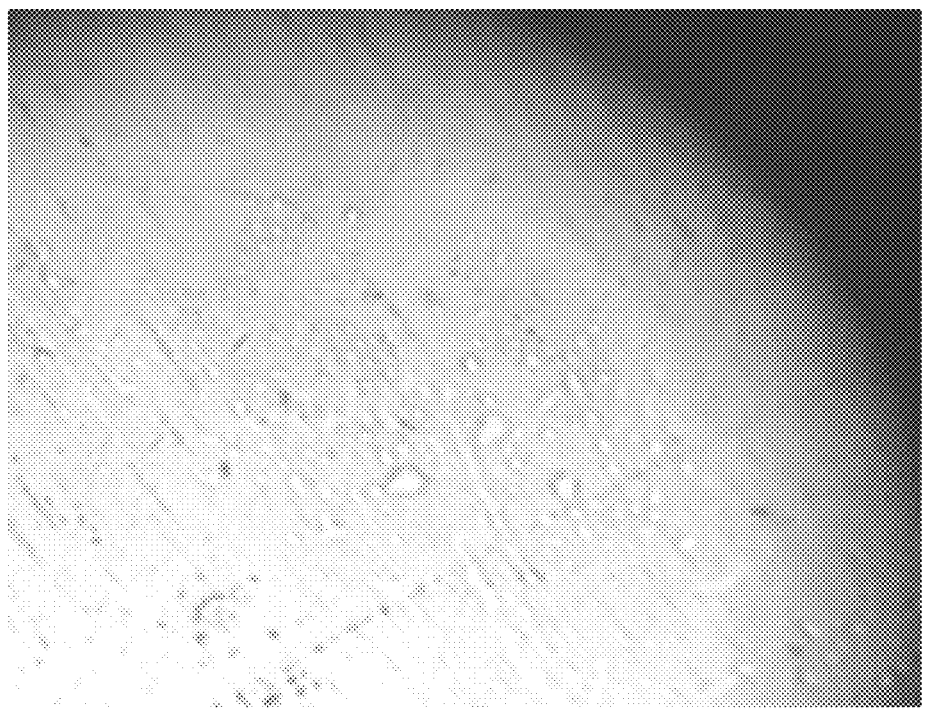

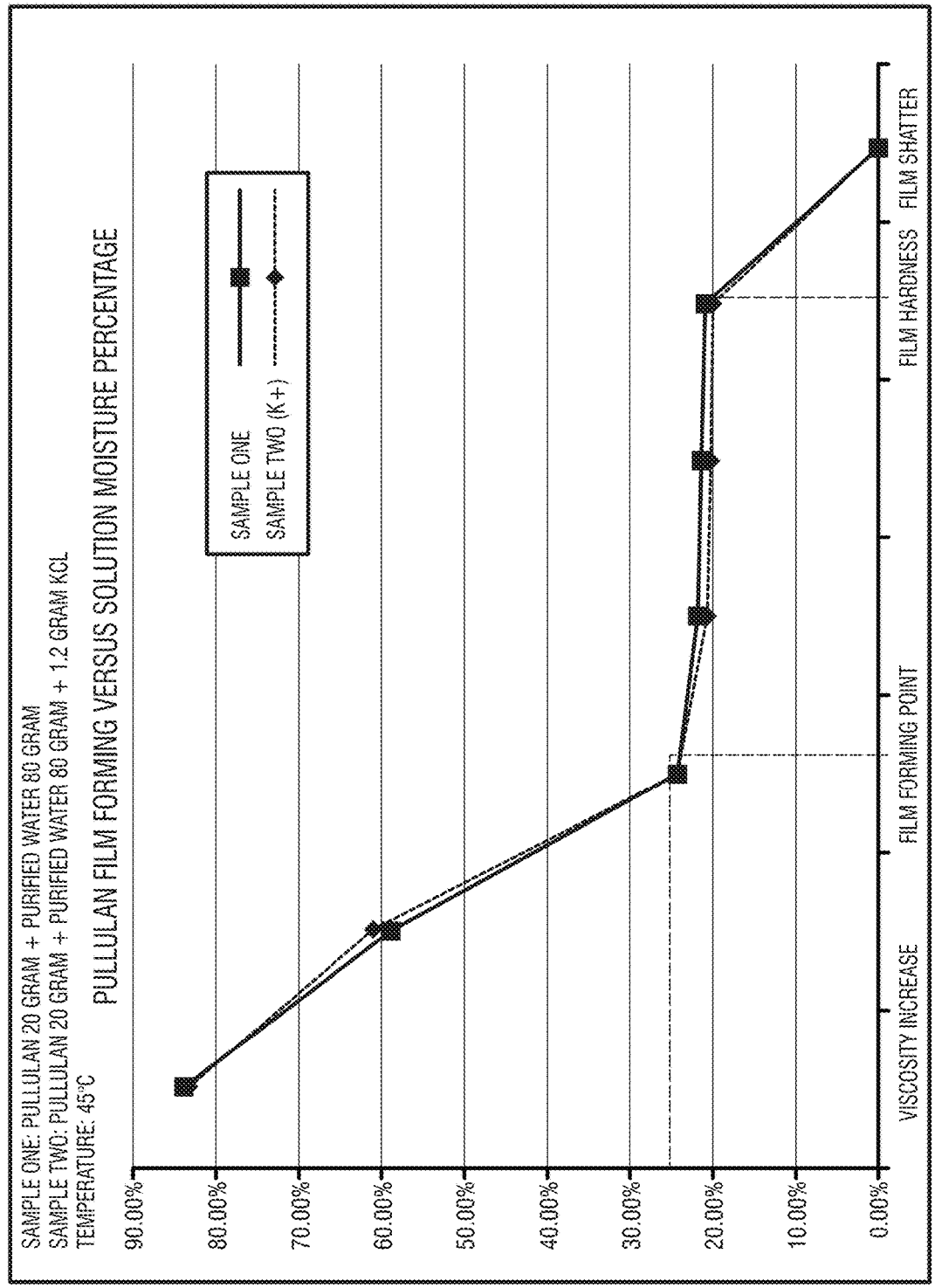

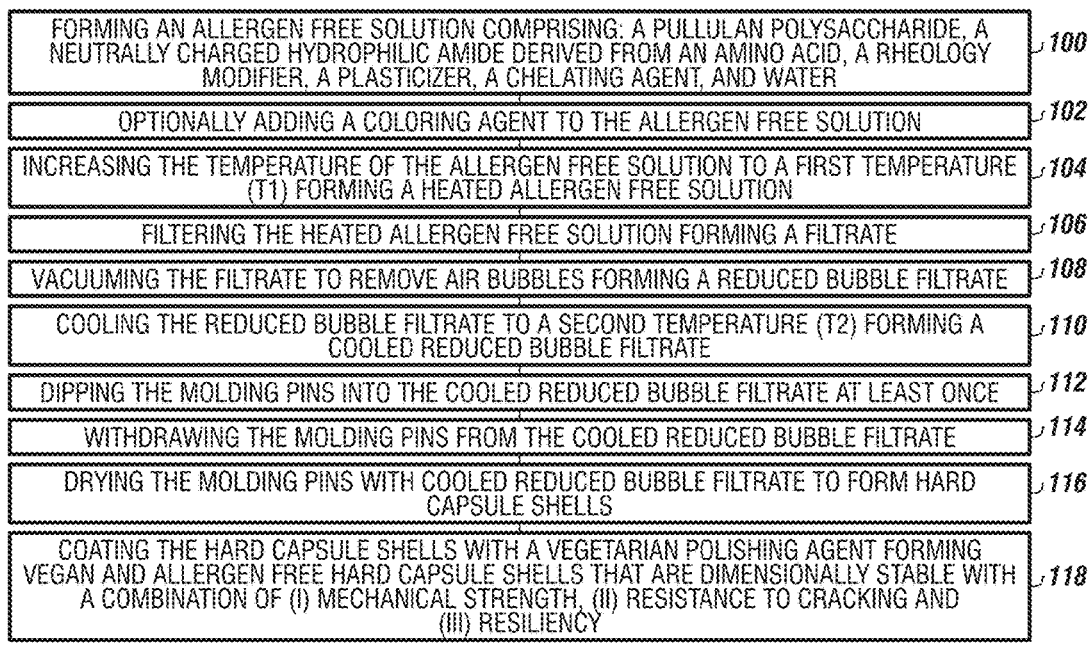

FIGURE 6

| INGREDIENTS | PUL-N FORMULA | PUL FORMULA |
|---|---|---|
| PULLULAN POWDER | 21% | 25% |
| CARRAGEENAN | 0.5% | 0.5% |
| L-GLUTAMINE | 4% | - |
| LECITHIN | 0.2% | 0.2% |
| EDTA | 0.1% | 0.1% |
| PURIFIED WATER | 74.2% | 74.2% |

FIGURE 7

| INGREDIENTS | PUL-N FORMULA | PUL FORMULA |
|---|---|---|
| PULLULAN POWDER | 21% | 25% |
| CARRAGEENAN | 0.5% | 0.5% |
| L-ASPARAGINES | 4% | - |
| LECITHIN | 0.2% | 0.2% |
| EDTA | 0.1% | 0.1% |
| PURIFIED WATER | 74.2% | 74.2% |

FIGURE 8

| INGREDIENTS | PUL-N FORMULA | PUL FORMULA |
|---|---|---|
| PULLULAN POWDER | 17% | 25% |
| CARRAGEENAN | 1.5% | 0.5% |
| L-GLUTAMINE | 7% | - |
| LECITHIN | 0.2% | 0.2% |
| EDTA | 0.1% | 0.1% |
| PURIFIED WATER | 74.2% | 74.2% |

FIGURE 9

| INGREDIENTS | PUL-N FORMULA | PUL FORMULA |
|---|---|---|
| PULLULAN POWDER | 23% | 25% |
| CARRAGEENAN | - | 0.5% |
| POTASSIUM ALGINATES | 0.3% | |
| L-ASPARAGINES | 3% | - |
| LECITHIN | 0.3% | 0.2% |
| EDTA | 0.1% | 0.1% |
| PURIFIED WATER | 73.3% | 74.2% |

FIGURE 10

| INGREDIENTS | PUL-N FORMULA | PUL FORMULA |
|---|---|---|
| PULLULAN POWDER | 35% | 25% |
| GELLAN GUM | 0.1% | |
| CARRAGEENAN | | 0.5% |
| L-GLUTAMINE | 0.5% | - |
| LECITHIN | 1.5% | 0.2% |
| EDTA | 0.01% | 0.1% |
| PURIFIED WATER | 62.89% | 74.2% |

FIGURE 11

| INGREDIENTS | PUL-N FORMULA | PUL FORMULA |
|---|---|---|
| PULLULAN POWDER | 20% | 25% |
| PECTIN | 0.3% | - |
| CARRAGEENAN | 0.2% | 0.5% |
| L-GLUTAMINE | 5% | - |
| LECITHIN | 0.2% | 0.2% |
| EDTA | 0.2% | 0.1% |
| PURIFIED WATER | 74.1% | 74.2% |

FIGURE 12

| INGREDIENTS | PUL-N FORMULA | PUL FORMULA |
|---|---|---|
| PULLULAN POWDER | 21% | 25% |
| CARRAGEENAN | 0.5% | 0.5 |
| L-GLUTAMINE | 6% | - |
| LECITHIN | 0.2% | 0.2% |
| EDTA | 0.1% | 0.1% |
| PURIFIED WATER | 72.2% | 74.2% |

FIGURE 13

| INGREDIENTS | PUL-N FORMULA | PUL FORMULA |
|---|---|---|
| PULLULAN POWDER | 22% | 25% |
| CARRAGEENAN | | 0.5% |
| GELLAN GUM | 0.3% | - |
| L-ASPARAGINES | 4% | - |
| LECITHIN | 0.2% | 0.2% |
| EDTA | 0.1% | 0.1% |
| PURIFIED WATER | 73.4% | 74.2% |

FIGURE 14

| INGREDIENTS | PUL-N FORMULA | PUL FORMULA |
|---|---|---|
| PULLULAN POWDER | 22% | 25% |
| CARRAGEENAN | - | 0.5% |
| GELLAN GUM | 0.3% | - |
| L-GLUTAMINE | 5% | - |
| GLYCERIN | 0.2% | 0.2% |
| EDTA | 0.1% | 0.1% |
| PURIFIED WATER | 72.4% | 74.2% |

FIGURE 15

| INGREDIENTS | PUL-N FORMULA | PUL FORMULA |
|---|---|---|
| PULLULAN POWDER | 22% | 25% |
| XANTHN GUM | 0.2% | - |
| POTASSIUM ALGINATE | 0.4% | - |
| CARRAGEENAN | - | 0.5% |
| L-GLUTAMINE | 7% | - |
| LECITHIN | 0.2% | 0.2% |
| EDTA | 0.1% | 0.1% |
| PURIFIED WATER | 70.1% | 74.2% |

FIGURE 16

| INGREDIENTS | PUL-N FORMULA | PUL FORMULA |
|---|---|---|
| PULLULAN POWDER | 23% | 25% |
| CARRAGEENAN | 0.5% | 0.5% |
| L-GLUTAMINE | 5% | - |
| GLYCERIN | 0.1% | 0.1% |
| EDTA | 0.1% | 0.1% |
| TITANIUM DIOXIDE | 0.6% | 0.6% |
| PURIFIED WATER | 70.7% | 73.7% |

FIGURE 17

| INGREDIENTS | PUL-N FORMULA | PUL FORMULA |
|---|---|---|
| PULLULAN POWDER | 24% | 24.8% |
| CARRAGEENAN | 0.5% | 0.5% |
| L-GLUTAMINE | 5% | - |
| LECITHIN | 0.2% | 0.2% |
| EDTA | 0.1% | 0.1% |
| TITANIUM DIOXIDE | 0.2% | 0.2% |
| CHLOROPHYLLIN | 0.1% | 0.1% |
| PURIFIED WATER | 70.9% | 74.1% |

DIP MOLDING PROCESS FOR THE MANUFACTURE OF HARD CAPSULE SHELLS

FIELD

The current embodiments generally relate to a dip molding process for the manufacture of hard shell capsules made of polysaccharides for the use in pharmaceuticals and food.

BACKGROUND

There is a need in the art to overcome drawbacks of conventional polysaccharide film compositions to make hard shell capsules for use in the pharmaceutical and vitamin supplement industries.

A need exists to reduce the breakage of polysaccharide films used to make hard shell capsules.

A further need exists to overcome spot mechanical weakness of polysaccharides that result from clumping, which is attributable to the use of non-dispersed ultra large molecules of pullulan powder.

A further need exists to accelerate the manufacturing process and improve its efficiency in order to reduce the high production cost for polysaccharides capsules.

The present embodiments meet these needs.

BRIEF DESCRIPTION OF THE DRAWINGS

The detailed description will be better understood in conjunction with the accompanying drawings as follows:

FIG. 1 depicts a photo of a microscopic view of a hard capsule shell surface with a weak spot according to one or more embodiments.

FIG. 2 depicts a photo of a microscopic view of a smooth, improved film surface of a hard capsule shell according to one or more embodiments.

FIG. 3 depicts a film formation and moisture chart according to one or more embodiments.

FIG. 4 depicts a process according to one or more embodiments.

FIG. 6 shows ingredients for a Pullulan film with the formula of Example 1.

FIG. 7 shows ingredients for a Pullulan film with the formula of Example 2.

FIG. 8 shows ingredients for a Pullulan film with the formula of Example 3.

FIG. 9 shows ingredients for a Pullulan film with the formula of Example 4.

FIG. 10 shows ingredients for a Pullulan film with the formula of Example 5.

FIG. 11 shows ingredients for a Pullulan film with the formula of Example 6.

FIG. 12 shows ingredients for a Pullulan film with the formula of Example 7.

FIG. 13 shows ingredients for a Pullulan film with the formula of Example 8.

FIG. 14 shows ingredients for a Pullulan film with the formula of Example 9.

FIG. 15 shows ingredients for a Pullulan film with the formula of Example 10.

FIG. 16 shows ingredients for a Pullulan film with the formula of Example 11.

FIG. 17 shows ingredients for a Pullulan film with the formula of Example 12.

Figure 5A:
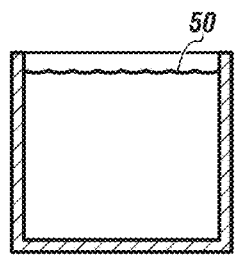
FIGS. 5A-5J depict the sequence of steps of forming a vegan allergen free capsules according to one or more embodiments.

The present embodiments are detailed below with reference to the listed Figures.

DETAILED DESCRIPTION OF THE EMBODIMENTS

Before explaining the present embodiments in detail, it is to be understood that the process and method are not limited to the particular embodiments and that it can be practiced or carried out in various ways.

The embodiments relate to a dip molding process for the manufacture of allergen free hard capsule shell.

The allergen free solution can be formed of (i) about 17 weight percent to about 35 weight percent based on the total weight of the allergen free solution of pullulan polysaccharide with no more than 0.5 percent of the pullulan polysaccharide with a molecular weight greater than 810 kDa, (ii) 0.5 weight percent to about 7 weight percent based on the total weight of the allergen free solution of a neutrally charged hydrophilic amide derived from an amino acid, (iii) 0.1 weight percent to about 1.5 weight percent based on the total weight of the allergen free solution of a rheology modifier, (iv) 0.1 weight percent to about 1.5 weight percent based on the total weight of the allergen free solution of a plasticizer, (v) 0.01 weight percent to about 0.2 weight percent based on the total weight of the allergen free solution of a chelating agent, and a quantity sufficient (Q.S.) amount of water, wherein Q.S. stands for the conventional chemical term "quantity sufficient" to create a liquid solution of the powder components in the liquid.

The temperature of the allergen free solution is increased to a temperature ranging from about 80 degrees Celsius to about 85 degrees Celsius forming a heated allergen free solution.

The heated allergen free solution is filtered using a woven synthetic cloth filter having a pore size from 10 microns to 20 microns and a porosity ranging from 45 percent to 65 percent forming a filtrate.

The filtrate is then vacuumed to remove from 98 percent to 99 percent of air bubbles in the filtrate forming a reduced bubble filtrate.

The reduced bubble filtrate is then cooled until the reduced bubble filtrate drops in temperature from about 40 degrees to 50 degrees Celsius forming a cooled filtrate.

Molding pins are then dipped into the cooled reduced bubble filtrate. The cooled reduced bubble filtrate adheres to the molding pins which have different diameters.

Next, the molding pins are withdrawn from the cooled filtrate.

Then cooled filtrate adhered to the molding pins are dried by quickly removing moisture to its moisture-induced setting point (indicated in FIG. 3), and the cooled reduced bubble free filtrate will change from liquid phase into a solid gel phase. The solid gel will further change to harden to a hard capsule after further drying.

The hard capsule shells then are cut to size, and stripped from dipping pins and form pre-lock capsule shells.

Then hard capsule shells are coated with a vegetarian polishing agent forming vegan and allergen free hard capsules that are dimensionally stable with a combination of (i) mechanical strength, (ii) resistance to cracking and (iii) resiliency, and wherein the created vegan and allergen free hard capsules have a body and cap that easily engage while producing an oxygen barrier for product.

In embodiments, the following words, phrases, and symbols are generally intended to have the meanings as set forth below, except to the extent that the context in which they are used indicates otherwise.

The term "about" as used herein is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

The term "allergen free" refers to the final hard capsules being free of the particular components listed herein: sodium lauryl sulfate, cocoamides, dioctyl sodium sulfosuccinate (DDS), benzalkonium chloride, benzethonium chloride, cetrimide (trimethyltetradecylammonium bromide), fatty acid sugar esters, glyceryl monooleate, polyoxyethylene sorbitan fatty acid esters, polyvinyl alcohol, dimethylpolysiloxane.

The term "capsule" as used herein can refer to either empty or filled capsule shells whereas "shell" specifically refers to an empty capsule. Since the hard capsule shells described herein can be filled with substances in liquid form, the hard capsules may be sealed or banded according to conventional techniques. Alternatively, the hard capsule shells can be manufactured to have a specific capsule shell design that provides certain advantages over conventional techniques, e.g., the ability to pre-lock empty caps and bodies, or completing the filling steps in a different location, or at a specific time.

The term "chelating agent" as used herein can refer to non-toxic to human ingredients that functionally remove cation(s) in solution to prevent interaction of cations interacting with rheology modifying agents. Preferred chelating agents are lecithin and ethylenediaminetetraacetic acid (ETDA) or salts.

The term "coloring agent" as used herein can refer to one or more pharmaceutically acceptable agents, food acceptable coloring agents, or mixtures thereof. The coloring agents may be selected from azo-, quinophthalone-, triphenylmethane-, xanthene- or indigoid dyes, iron oxides or hydroxides, titanium dioxide, or natural dyes and mixtures thereof. Further examples are patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, chlorophyllin, canthaxanthin, caramel, betanin and Candurin™ pearlescent pigments. Candurin™ is manufactured and marketed by Merck KGaA®, of Darmstadt, Germany, and consist of titanium dioxide and/or iron oxide—approved food and pharmaceutical colorants in many countries—and potassium aluminum silicate as color carrier.

In embodiments, the pharmaceutically acceptable coloring agents, food acceptable coloring agents, or mixtures thereof are present in an amount ranging from about 0 to about 5 percent by weight, e.g., from about 0 to about 2.5 percent by weight, and from about 0 to about 1.5 percent by weight over the total weight of the aqueous composition.

The term "film forming solution" as used herein can refer to material used as base for hard capsule shells. Examples include HPMC (e.g. HPMC types 2910, 2906 and/or 2208 as defined in USP30-NF25), gelatin, pullulan, PVA and non-enteric starch derivatives, such as hydroxypropyl starch.

The term "hard capsules" as used herein can refer to capsules intended for oral administration to human or animal subjects. The hard capsules described herein can be manufactured using different processes, such as the dip molding processes discussed below as well as the use of conventional equipment. As is described in detail below, pin molds can be dipped into an aqueous-based film forming solution and subsequently withdrawn. The film formed on the molding pins surface can then be dried, stripped off the pins and cut to a desired length, thereby obtaining the capsules caps and bodies. Normally, caps and bodies have a side wall, an open end and a closed end. The length of the side wall of each of said parts is generally greater than the capsule diameter. The capsule caps and bodies can be telescopically joined together so as to make their side walls partially overlap and obtain a hard capsule shell.

The term "neutrally charged hydrophilic amide" as used herein can refer to amides compounds that are neither positively nor negatively charged, are soluble in water, and are hydrophilic. In embodiments, the neutrally charged hydrophilic amides derived from amino acids are glutamine and/or asparagines, preferably L-glutamine and/or L-asparagine. The amount of neutrally charged hydrophilic amides derived from amino acids can be in the amount that is from 0.5 percent to 7 percent in film forming solution.

The term "optional" or "optionally" as used herein can mean that the subsequently described event or circumstance may or may not occur, and that the description includes instances where the event or circumstance occurs and instances in which it does not.

The term "pullulan polysaccharide" can refer to polysaccharide polymer consisting of maltotriose units, also known as $\alpha$-1,4; $\alpha$-1,6-glucan. Three glucose units in maltotriose are connected by an $\alpha$-1,4 glycosidic bond, whereas consecutive maltotriose units are connected to each other by an $\alpha$-1,6 glycosidic bond.

The term "rheology modifier" as used herein can refer alginates, agar gum, guar gum, locust bean gum, carrageenan, tara gum, gum arabic, ghatti gum, *Khaya grandifolia* gum, tragacanth gum, karaya gum, pectin, arabian (araban), xanthan, gellen, starch, Konjac mannan, galactomannan, funoran, and other exocellular polysaccharides. The amount of rheology modifier can preferably be in the range of 0.1 to 1.5 percent by weight.

The term "weight percent" as used herein can mean weight as a percentage of the total weight.

The term "moisture setting system" as used herein can refer to the start of moisture induced solidifying of pullulan solution; pullulan solution will start changing from liquid solution phase into solid gel phase as moisture in solution is reduced to around 20 percent. After the setting starts, the pullulan solution becomes immobile and will retain its shape at the point of setting. The solid gel will be dried into solid film as moisture is further being reduced.

Now turning to the Figures, FIG. 1 depicts a photo of a microscopic view of a hard capsule shell surface with a weak spot according to one or more embodiments.

A microscopic view of a capsule 1 surface with a weak spot 2 is illustrated. The weak spot 2 can be about 6 microns to about 30 microns thinner than normal/preferred capsule thickness.

Weak spots in film make the film more susceptible to mechanical tearing, pressing and twisting comparing with film with no such weak spots, and resulting elevated chances of breakage of the film and capsules formed by such film during normal usage operation of such film and capsules.

The amount of such weak spots depends on the percentage of ultra large polysaccharides in the pullulan powder, the blending force during the solution formation process, and the sitting time of the solution. In industrial settings of capsule manufacturing, the blending force is generally applied as less as possible to reduce air bubbles. The sitting time of solution is also timed. Therefore, the amount of weak spots in pullulan film is directly linked to the percentage of ultra large molecules of pullulan powder.

FIG. 2 depicts a photo of a microscopic view of a smooth, improved film surface of a hard capsule shell according to one or more embodiments.

FIG. 3 depicts a moisture induced setting system where film formation in relation to percentage of moisture is charted according to one or more embodiments.

More specifically, the Figure shows sample one and sample two over time as viscosity increases against moisture percentage. As the moisture percentage drop to a given point, the solution starts to gel and the solution phase changes into solid gel phase. This unique moisture-setting property can be utilized in similar manner as to thermal-setting properties of gelatin. Only instead of changing the temperatures in gelatin solution to trigger setting, reducing moisture in pullulan solution will trigger the setting. This moisture—gelling properties of pullulan is utilized to manufacturing pullulan capsules in the embodiments.

The capsules made with the formula of sample one are also subjected to automatic high speed encapsulation with maximum vacuum power and maximum volume filling on an NJP 1200 automatic encapsulation machine to test the capsules' improvement of machine ability. The filling material can be calcium carbonate powder, and the reduction of number of broken, deformed capsules per 10,000 capsules is recorded as indicator of improvements.

In embodiments, the aqueous solution of film compositions can be used for the manufacturing of hard capsules by dip molding process without thermo setting system like one used by the traditional process of making hard gelatin capsules. The solution viscosity and rapid reduction of moisture level are used to control the flow down of the solution from the dipping pins after dipping. Rather than using temperature drop after dipping the molds into the solution to trigger the starting of thermos-setting process like the "gum plus cations" setting system, the moisture—setting properties of pullulan polysaccharides that naturally exists are used, as illustrated in FIG. 3. The shape and the film thickness of capsules are controlled by combinations of rheological modifiers and moisture removal process rather than by "thermal-setting". The advantage of the viscosity plus "moisture-setting" method is that temperature can remain high after the dipping process. The high temperature can speed up the film forming process and film drying process. Therefore, the rate of moisture removal is improved, and the production efficiency can be improved in comparison with production efficiency using "thermal setting" system, wherein thermal setting requires the temperature to be dropped below the "setting temperature" at all times during the drying process, because thermal setting can be reversible.

In embodiments, the film forms solutions and the unit dosage forms made from it can be used for providing a protective film for agrochemicals, seeds, herbs, foodstuffs, dyestuffs, pharmaceuticals and flavoring agents. The container can be preferably capsules having a capsule body and a capsule cap. The capsule halves of the capsules can be preferably sealed with one or more layers of the film forming solution of the present embodiments.

In addition to the new composition, the present embodiments specifically omit the use of select surfactants in the aqueous composition.

Gliding of the capsule is enhanced using natural vegan plant wax after capsules are manufactured by the dipping process.

Plant vegan wax, such as carnauba wax, in fine powder can be used which has a particle size of 200 US mesh, in the amount of 0.1 percent to 1.0 percent to be sprayed on to the capsules made with present composition. This manufacturing process eliminates the need for surfactants required to improve pullulan capsules gliding performance.

Further, the pullulan compositions can additionally contain lecithin, glycerin or sorbitol as a plasticizer.

In embodiments, the water of the aqueous composition can be purified in a manner that is acceptable for pharmaceutical uses as defined under USP purified water in USP32 and USP34-NF29. It will be understood that the aqueous composition described herein allows for non-aqueous solvents in trace amounts.

With these aqueous solutions, hard pullulan capsules can have improved mechanical strength and good flexibility during filling operation.

In embodiments, the hard capsule shells as described have a shell thickness (after drying to bring the water content of the shell from 9 percent to 16 percent by weight over the weight of the shell) from about 70 to about 250 μm, e.g., preferably at about 100 μm. Thus, in one embodiment, the shell thickness may range from about 70 μm to about 150 μm.

Typically, sealing or banding techniques can be used where these techniques are well-known to any skilled person in the field of capsules.

FIG. 4 depicts the process according to one or more embodiments.

The dip molding process for the manufacture of allergen free hard capsule shells can include, but is not limited to the steps described below. The process can be utilized by a person of ordinary skill in the industry, and is not limited to a particular order or sequence.

The process can include forming an allergen free solution, as shown in step 100.

The allergen solution can contain 17 weight percent to about 35 weight percent based on the total weight of the allergen free solution of pullulan polysaccharide with no more than 0.5 percent of the pullulan polysaccharide with a molecular weight greater than 810 kDa, 0.5 weight percent to about 7 weight percent based on the total weight of the allergen free solution of a neutrally charged hydrophilic amide derived from an amino acid, 0.1 weight percent to about 1.5 weight percent based on the total weight of the allergen free solution of a rheology modifier, 0.1 weight percent to about 1.5 weight percent based on the total weight of the allergen free solution of a plasticizer, 0.01 weight percent to about 0.2 weight percent based on the total weight of the allergen free solution of a chelating agent, and a Q.S. amount of water.

In embodiments, a hard capsule shell can contain 65 weight percent to about 99 weight percent based on the total weight of an allergen free solution of pullulan polysaccharide with no more than 0.5% of the pullulan polysaccharide with a molecular weight greater than 810 kDa, 0.5 weight percent to about 15 weight percent based on the total weight of the allergen free solution of a neutrally charged hydrophilic amide derived from an amino acid, 0.3 weight percent to about 4.5 weight percent based on the total weight of the allergen free solution of a rheology modifier, 0.3 weight percent to about 4.5 weight percent based on the total weight of the allergen free solution of a plasticizer, 0.01 weight percent to about 0.6 weight percent based on the total weight of the allergen free solution of a chelating agent, and a quantity sufficient (Q.S.) amount of water The process can include optionally adding a coloring agent to the allergen free solution, as shown in step 102.

The process can include increasing the temperature of the allergen free solution to a first temperature (T1) forming a heated allergen free solution, as shown in step 104.

In embodiments, the temperature can range from about 80 degrees Celsius to about 85 degrees Celsius.

The process can include filtering the heated allergen free solution forming a filtrate as shown in step 106.

The heated allergen free solution can be filtered using a woven synthetic cloth filter having a pore size from 10 microns to 20 microns and a porosity ranging from 45 percent to 65 percent.

The process can include vacuuming the filtrate to remove from 98 percent to 99 percent of air bubbles in the filtrate forming a reduced bubble filtrate, as shown in step 108.

The process can include cooling the reduced bubble filtrate until the reduced bubble filtrate drops to a second temperature (T2) forming a cooled reduced bubble filtrate, as shown in step 110.

In embodiments, the temperature can range from 40 degrees Celsius to 50 degrees Celsius.

The process can include dipping the molding pins into the cooled reduced bubble filtrate at least once, as shown in step 112.

The process can include withdrawing the molding pins from the cooled reduced bubble filtrate, as shown in step 114.

The process can include drying the molding pins with cooled reduced bubble filtrate to quickly remove moisture to reach a moisture induced setting point to transform the cooled reduced bubble filtrate into a solid phase gel to form hard capsule shells, as shown step 116.

The process can include coating the hard capsule shells with a vegetarian polishing agent forming vegan and allergen free hard capsules that are dimensionally stable with a combination of (i) mechanical strength, (ii) resistance to cracking, and (iii) resiliency, as shown in step 118.

The created vegan and allergen free hard capsules have a body and cap that easily engage while producing an oxygen barrier for product.

FIGS. 5A-5J depict the sequence of steps of forming the vegan allergen free capsules containing an ingredient.

FIG. 5A depicts the allergen free solution 50 in a container.

Figure 5B:
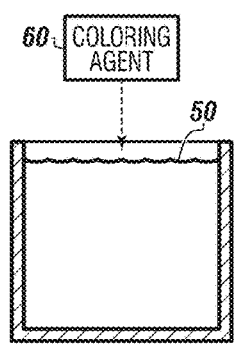

FIG. 5B depicts adding a coloring agent 60 to the allergen free solution 50.

Figure 5C:
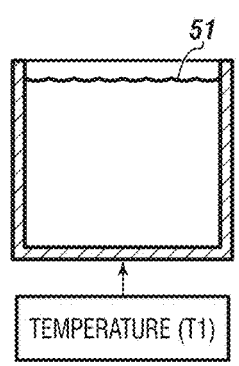

FIG. 5C depicts increasing the temperature (T1) of the allergen free solution from about 80 degrees Celsius to about 85 degrees Celsius forming a heated allergen free solution 51.

Figure 5D:
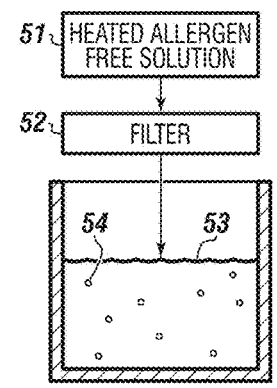

FIG. 5D depicts filtering the heated allergen free solution 51 using a woven synthetic cloth filter 52 with a pore size from 10 microns to 20 microns forming a filtrate 53 with air bubbles 54.

Figure 5E:
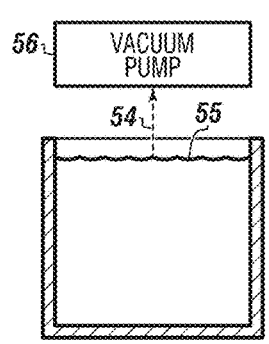

FIG. 5E depicts vacuuming the filtrate 53 to remove from 98 percent to 99 percent of air bubbles 54 in the filtrate using a vacuum pump 56 forming a reduced bubble filtrate.

Figure 5F:
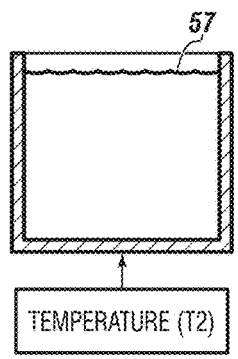

FIG. 5F depicts cooling the reduced bubble filtrate until the reduced bubble filtrate drops in temperature (T2) ranging from 40 degrees Celsius to 50 degrees Celsius forming a cooled reduced bubble filtrate 57.

Figure 5G:
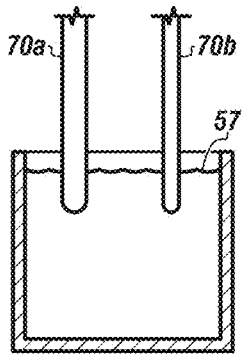

FIG. 5G depicts dipping the molding pins 70a and 70b into the cooled reduced bubble filtrate 57.

Figure 5H:
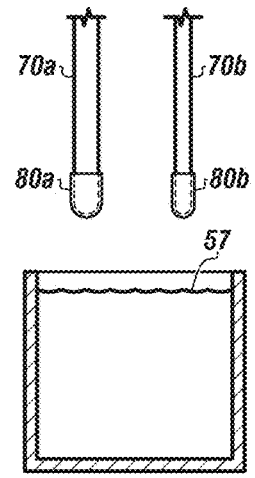

FIG. 5H depicts withdrawing the molding pins 70a and 70b from the cooled reduced bubble filtrate 57 having a layer of cooled filtrate 80a and 80b on each molding pin 70a and 70b respectively.

Figure 5I:
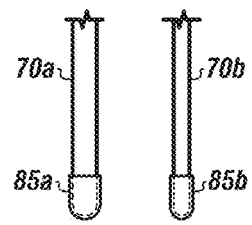

FIG. 5I shows the step of drying the molding pins 70a and 70b with cooled filtrate to form hard capsule shells 85a and 85b.

Figure 5J:
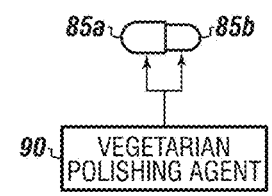

FIG. 5J depicts coating the hard capsule shells, a body 85a and a cap 85b with a vegetarian polishing agent 90 forming vegan and allergen free hard capsules that are dimensionally stable with a combination of (i) mechanical strength, (ii) resistance to cracking and (iii) resiliency, wherein the created vegan and allergen free hard capsules have a body and cap that easily engage while producing an oxygen barrier for product. The body and cap each have different diameters.

In embodiments, the dip molding process can use pullulan polysaccharide that has less than 0.1 weight percent with a molecular weight no greater than 810 kDa.

In embodiments, the dip molding process can use a rheology modifier that is at least one of: seaweed, seaweed extract, seed gums, plant exudates, natural fruit extracts, biosynthetic gums, starches, cellulosic material, food or pharmaceutical grade alginates, carrageenan, xanthan gum and combinations thereof.

In embodiments, the dip molding process can use a plasticizer selected from the group consisting of: natural plasticizer, synthetic plasticizer, glycerin, lecithin, sorbitol, and a glycerin derivative.

In embodiments of the dip molding process, the amino acid can be at least one of: an L-glutamine and an L-asparagine.

In embodiments, the dip molding process can use as the vegetarian polishing agent a plant wax, such as carnauba wax.

In embodiments, the dip molding process can use a pullulan polysaccharide produced from at least one of corn starch or tapioca starch.

In embodiments, the dip molding process can add a coloring agent in a range from about 0.001 percent to about 2 percent based upon the weight of the allergen free solution.

In embodiments, the dip molding process coloring agent can be at least one of azo-, quinophthalone-, triphenylmethane, xanthene- or indigoid dyes, iron oxides or hydroxides, titanium dioxide, natural dyes, and combinations thereof.

In embodiments, the dip molding process can involve at least one dipping of the molding pins.

In embodiments, the dip molding process can have the step of filling each hard capsule shell with at least one active ingredient.

In embodiments, the process can create a hard capsule shell.

In embodiments, the hard shell capsule can have at least one encapsulated active ingredient.

The amount of moisture in the hard capsule shell, as equilibrated with the relative humidity of the outside air, can range from about 2 percent to about 20 percent by weight of the total weight of the hard capsule shell.

In embodiments, at least one active ingredient in the hard capsule shell can be a solid, a semi-solid, or in liquid form.

EXAMPLES

The following includes but is not limited to examples of film forming solution usable for the manufacture of an allergen free capsule.

Example 1

Pullulan powder with less than 0.5 percent, preferably less than 0.1 percent ultra 5 large molecules, with the formula shown in FIG. 6:

The abbreviation "Pul-N formula" refers to pullulan new formulation

The abbreviation "Pul formula" refers to pullulan regular formulation.

In this example, all the identified ingredients are mixed for 21 minutes in a jacketed vat and then heated with hot water at a temperature of 100 degrees Celsius as an aqueous solution to a temperature of 80 degrees Celsius for 10 minutes. The heated and mixed aqueous solution is then agitated for about 20 minutes with a mechanical agitator having a plurality of blades, such as 2, at a low rpm, for gentle reduced bubble mixing to create a homogenous mixture with few air bubbles.

After creating the homogenous mixture, the homogenous mixture is then filtered through a woven synthetic cloth filter having a pore size of 10 microns.

The pores can be any number of shapes. The porosity of the filter can be 50 percent.

The filtrate is then allowed to cool using a jacketed vat with electrical cooler system or a similar cooling device, until the filtrate drops in temperature to 40 degrees Celsius in 2 hours forming a cooled filtrate.

The filtrate temperature drop should drop to the target temperature in a two hour window.

The cooled filtrate has air bubbles that are then removed using reduced pressure with a vacuum pump. The vacuum eliminates 98 percent of all air bubbles in the cooled filtrate. The air bubble free filtrate can be stored for later use.

The cooled filtrate is surfactant free, such as free of sodium lauryl sulfate.

Hard capsules are then formed using the stored air bubble free filtrate by one of various known dipping methods, such as using dipping pins and repeatedly dipping while cooled filtrate is maintained at a temperature from 40 degrees to 50 degrees Celsius, a thin layer of air bubble free filtrate will adhere on the surface of pins.

Then, quickly remove the moisture content of the air bubble free filtrate adhered on the pins by blowing hot and drying air. The air bubble free filtrate layer will start the moisture induced setting and will change from liquid phase into a solid gel phase. The solid gel phase will further harden to form a hard capsule after further drying. More specifically, in embodiments after dipping, the dipping pins are subjected to hot air for drying. The hot air can have a temperature of 44 degrees Celsius. The hot air can be blown onto the dipping pins from six different angles to dry the viscous pullulan solution in the shape of the dipping pins.

As soon as the surface pullulan forms a film, the pins with film are then moved into drying tunnels.

Air in the drying tunnels is maintained at a temperature of 43 degrees Celsius and a relative humidity of 15 percent.

The choice of temperature is based on information shown in FIG. 3, which shows the film formation and moisture chart.

The formed capsule body and cap are then removed from the dipping pins such as by cutting and stripping, and then joined into pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 1 have improved pullulan capsule film.

"Brittleness properties" of capsules is defined by calculating percentage of capsules that will crack, deform, unable to return to its original shape after dropping a 15 gram steel piece in a plastic cylinder at a height of 20 cm on each of randomly selected 20 capsules. Brittleness property is a collective indicator of mechanical strength, flexibility and resilience of capsules under mechanical stress.

The capsule(s) made according to embodiments of Example 1 have a brittleness property improved by about 36 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has an improved moisture retention property during storage at ambient temperature. The property to retain its original moisture level keeps the capsule flexible even when very dry ingredients are used inside the capsule for delivery to a subject, reducing chances of interaction between the capsules shell and the ingredient that is placed into the domed capsule. The moisture retention property enables the capsule to remain resistant to water withdrawal and adsorption of water into product contained in the capsule.

This moisture retention property prevents crosslinking and migration with product in the capsule. The moisture retention property prevents development of a brittle capsule that either can break or cause other product contamination.

Sodium lauryl sulfate or similar surfactants or gliding agent is not needed with this capsule formulation. Due to overall environmental issues and toxicity issues for people, the invention uses plant wax replacing the need for the sodium lauryl sulfate.

The embodiments satisfy a need for an animal ingredient free natural composition. This is a non-gelatin capsule that vegans can take. Hydroxy methyl propyl cellulose is a semi-synthetic fiber and is not a natural product. This formulation satisfies a need for all natural ingredients capsule desired by the consumer. This formulation provides a lower environmental impact on society and the environment overall.

Example 2

FIG. 7 shows the ingredients for the Pullulan powder with the formula of Example 2:

In this example, all the identified ingredients are mixed for 20 minutes in a jacketed vat and then heated with hot water at a temperature of 100 degrees Celsius as an aqueous solution to a temperature of 82 degrees Celsius for 20 minutes. The heated and mixed aqueous solution is then agitated for about 20 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping while cooled filtrate is maintained at a temperature from 40 degrees to 50 degrees Celsius, a thin layer of air bubble free filtrate will adhere on the surface of pins.

Then, quickly remove the moisture content of the air bubble free filtrate adhered on the pins by blowing hot and drying air. The air bubble free filtrate layer will start the moisture induced setting and will change from liquid phase into a solid gel phase. The solid gel phase will further change to harden to a hard capsule after further drying. More specifically, after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature from 39 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 2 have improved pullulan capsule film.

The capsule(s) made according to embodiments of Example 2 have a brittleness property improved by about 37 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 23 percent.

Example 3

FIG. 8 shows the ingredients for the Pullulan film with the formula of Example 3:

In this example, all the identified ingredients are mixed for 20 minutes in a jacketed vat and then heated with hot water at a temperature of 100 degrees Celsius as an aqueous solution to a temperature of 82 degrees Celsius for 20 minutes. The heated and mixed aqueous solution is then agitated for about 20 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule, More specifically, in embodiments after dipping, the dipping pins are subjected to hot air for drying. The hot air can have a temperature of 44 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature from 36 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 3 have improved pullulan capsule film.

The capsule(s) made according to embodiments of Example 3 have a brittleness property improved by about 14 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 6 percent.

Example 4

FIG. 9 shows the ingredients for the Pullulan film with the formula of Example 4:

In this example, all the identified ingredients are mixed from 20 minutes in a jacketed vat and then heated with hot water at a temperature between 100 degrees Celsius as an aqueous solution to a temperature from 82 degrees Celsius for 20 minutes. The heated and mixed aqueous solution is then agitated for about 20 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule, More specifically, in embodiments after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature of 39 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 4 have improved pullulan capsule film.

The capsule(s) made according to embodiments of Example 4 have a brittleness property improved by about 26 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 16 percent.

Example 5

FIG. 10 shows the ingredients for the Pullulan film with the formula of Example 5:

In this example, all the identified ingredients are mixed for 20 minutes in a jacketed vat and then heated with hot water at a temperature of 100 degrees Celsius as an aqueous solution to a temperature of 82 degrees Celsius for 20 minutes. The heated and mixed aqueous solution is then agitated for about 30 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to between 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule.

More specifically, in embodiments after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature of 39 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 5 have improved pullulan capsule film.

The capsule(s) made according to embodiments of Example 5 have a brittleness property improved by about 9 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 4 percent.

Example 6

FIG. 11 shows the ingredients for the Pullulan film with the formula of Example 6:

In this example, all the identified ingredients are mixed for 20 minutes in a jacketed vat and then heated with hot water at a temperature of 100 degrees Celsius as an aqueous solution to a temperature of 82 degrees Celsius for 20 minutes. The heated and mixed aqueous solution is then agitated for about 20 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to between 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule, More specifically, in embodiments after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature from 39 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 6 have improved pullulan capsule film.

The capsule(s) made according to embodiments of Example 6 have a brittleness property improved by about 26 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 16 percent.

Example 7

FIG. 12 shows the ingredients for the Pullulan film with the formula of Example 7:

In this example, all the identified ingredients are mixed for 20 minutes in a jacketed vat and then heated with hot water at a temperature of 100 degrees Celsius as an aqueous solution to a temperature of 82 degrees Celsius for 20 minutes. The heated and mixed aqueous solution is then agitated for about 25 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule.

More specifically, after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature of 39 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 7 have improved pullulan capsule film.

The capsule(s) made according to embodiments of Example 7 have a brittleness property improved by about 35 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 18 percent.

Example 8

FIG. 13 shows the ingredients for the Pullulan film with the formula of Example 8:

In this example, all the identified ingredients are mixed for 20 minutes in a jacketed vat and then heated with hot water at a temperature of 100 degrees Celsius as an aqueous solution to a temperature of 82 degrees Celsius for 20 minutes. The heated and mixed aqueous solution is then agitated for about 20 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule.

More specifically, in embodiments after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature of 39 degrees Celsius and a relative humidity from 15 percent to 28 percent.

The choice of temperature is based on information shown in FIG. 3, which shows the film formation and moisture chart.

The formed capsule body and cap are then removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 8 have improved pullulan capsule film.

The capsule(s) made according to embodiments of Example 8 have a brittleness property improved by about 41 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 23 percent.

Example 9

FIG. 14 shows the ingredients for the Pullulan film with the formula of Example 9:

In this example, all the identified ingredients are mixed for 20 minutes in a jacketed vat and then heated with hot water at a temperature of 100 degrees Celsius as an aqueous solution to a temperature of 82 degrees Celsius for 20 minutes. The heated and mixed aqueous solution is then agitated for about 25 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule.

More specifically, in embodiments after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature of 39 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 9 have improved pullulan capsule film.

The capsule(s) made according to embodiments of Example 9 have a brittleness property improved by about 31 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 20 percent.

Example 10

FIG. 15 shows the ingredients for the Pullulan film with the formula of Example 10:

In this example, all the identified ingredients are mixed for 20 minutes in a jacketed vat and then heated with hot water at a temperature of 100 degrees Celsius as an aqueous solution to a temperature of 82 degrees Celsius for 20 minutes. The heated and mixed aqueous solution is then agitated with a mechanical agitator for about 30 minutes having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule.

More specifically, in embodiments after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature from 39 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 10 have improved pullulan capsule film.

The capsule(s) made according to embodiments of Example 10 have a brittleness property improved by about 38 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 21 percent.

Example 11

FIG. 16 shows the ingredients for the Pullulan film with the formula of Example 11:

In this example, all the identified ingredients are mixed for 20 minutes in a jacketed vat and then heated with hot water at a temperature of 100 degrees Celsius as an aqueous solution to a temperature of 82 degrees Celsius for 20 minutes. The heated and mixed aqueous solution is then agitated for about 30 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule, More specifically, in embodiments after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature from 39 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 11 have improved pullulan capsule film.

The capsule(s) made according to embodiments of Example 11 have a brittleness property improved by about 33 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 16 percent.

Example 12

FIG. 17 shows the ingredients for the Pullulan film with the formula of Example 12:

In this example, all the identified ingredients are mixed for 20 minutes in a jacketed vat and then heated with hot water at a temperature between 100 degrees Celsius as an aqueous solution to a temperature of 82 degrees Celsius for 20 minutes. The heated and mixed aqueous solution is then agitated for about 30 minutes with a mechanical agitator having a plurality of blades (2) for gentle reduced bubble mixing to create a homogenous mixture with few air bubbles.

After creating the homogenous mixture, the homogenous mixture is then filtered through a woven synthetic cloth filter having a pore size from 20 microns. The pores can be any number of shapes. The porosity of the filter can range from 45 percent to 65 percent.

The filtrate has air bubbles that are then removed using reduced pressure with a vacuum pump. The vacuum eliminates from 98 percent to 99 percent of all air bubbles in the filtrate. The air bubble free filtrate can be stored for later use.

The filtrate is then allowed to cool using a jacketed vat with electrical cooler system or a similar cooling device, until the filtrate drops in temperature to 45 degrees Celsius forming a cooled filtrate.

The filtrate temperature drop should drop to the target temperature in a two hour window.

The cooled filtrate is surfactant free, such as free of sodium lauryl sulfate.

Hard capsules are then formed using the stored air bubble free filtrate by one of various known dipping methods, such as using dipping pins and repeatedly dipping and drying the pins into the air bubble free filtrate allowing the layers to harden to a hard capsule.

More specifically, after dipping, the dipping pins are subjected to hot air for drying. The hot air can have a temperature of 42 degrees Celsius. The hot air can be blown onto the dipping pins from four different angles to dry the viscous pullulan solution in the shape of the dipping pins.

As soon as the surface pullulan forms a film, the pins with film are then moved into drying tunnels.

Air in the drying tunnels is maintained at a temperature from 39 degrees Celsius and a relative humidity from 15 percent to 28 percent.

The choice of temperature is based on information shown in FIG. 3, which shows the film formation and moisture chart.

The formed capsule body and cap are the removed from the dipping pins such as by cutting and stripping, and then joined into a pre-lock position.

Pre-locked pullulan capsules are sprayed with plant based wax, such as carnauba wax to improve gliding performance on an encapsulation machine and also improve flow-ability during production process.

The capsule(s) made according to embodiments of Example 12 have improved pullulan capsule film.

The capsule(s) made according to embodiments of Example 12 have a brittleness property improved by about 31 percent at ambient temperatures.

No setting agent is needed in this formulation. No trigger setting agents are needed in this film.

Additionally, this formulation requires no surfactant to maintain the suspension of ultra large molecules, or as a polishing agent.

The formed capsule of this formation has improved moisture retention property during storage at ambient temperature. The moisture loss at ambient temperature reduced by 16 percent.

While these embodiments have been described with emphasis on the embodiments, it should be understood that within the scope of the appended claims, the embodiments might be practiced other than as specifically described herein.

What is claimed is:

1. A dip molding process for manufacture of allergen free hard capsule shells comprising:
   a. forming an allergen free solution of:
      (i) 17 weight percent to 35 weight percent based on the total weight of the allergen free solution of pullulan polysaccharide with no more than 0.5 percent of the pullulan polysaccharide with a molecular weight greater than 810 kDa;
      (ii) 0.5 weight percent to 7 weight percent based on the total weight of the allergen free solution of a neutrally charged hydrophilic amide derived from an amino acid;

(iii) 0.1 weight percent to 1.5 weight percent based on the total weight of the allergen free solution of a rheology modifier;
(iv) 0.1 weight percent to 1.5 weight percent based on the total weight of the allergen free solution of a plasticizer;
(v) 0.01 weight percent to about 0.2 weight percent based on the total weight of the allergen free solution of a chelating agent; and
(vi) a quantity sufficient (Q.S.) amount of water;
b. increasing the temperature of the allergen free solution to a temperature ranging from 80 degrees Celsius to 85 degrees Celsius forming a heated allergen free solution;
c. filtering the heated allergen free solution using a woven synthetic cloth filter having a pore size from 10 microns to 20 microns and a porosity ranging from 45 percent to 65 percent forming a filtrate;
d. vacuuming the filtrate to remove from 98 percent to 99 percent of air bubbles in the filtrate forming a reduced bubble filtrate;
e. cooling the reduced bubble filtrate until the reduced bubble filtrate drops in temperature of 40 degrees Celsius to 50 degrees Celsius forming a cooled reduced bubble filtrate;
f. dipping molding pins into the cooled reduced bubble filtrate while cooled reduced bubble filtrate is maintained at a temperature from 40 degrees Celsius to 50 degrees Celsius;
g. withdrawing the molding pins from the cooled reduced bubble filtrate;
h. drying the molding pins with the cooled reduced bubble filtrate to quickly remove moisture to reach a moisture-induced setting point to transform the cooled reduced bubble filtrate from a liquid phase into a solid phase gel, wherein the solid phase gel on the molding pins is not thermal sensitive or thermal reversible, and permits drying continuously in higher temperatures to form the allergen free hard capsule shells; and
i. coating the allergen free hard capsule shells with a vegetarian polishing agent forming vegan and allergen free hard capsules that are dimensionally stable with a combination of mechanical strength, resistance to cracking and resiliency, and wherein the created vegan and allergen free hard capsules have a body and a cap that easily engage while producing an oxygen barrier for product.

2. The dip molding process of claim 1, wherein the pullulan polysaccharide comprises less than 0.1 weight percent with a molecular weight no greater than 810 kDa.

3. The dip molding process of claim 1, wherein the rheology modifier is at least one of: seaweed, seaweed extract, seed gums, plant exudates, natural fruit extracts, biosynthetic gums, starches, cellulosic material, food or pharmaceutical grade alginates, carrageenan, xanthan gum and combinations thereof.

4. The dip molding process of claim 1, wherein the plasticizer is selected from the group consisting of: a natural plasticizer, a synthetic plasticizer, a glycerin, a lecithin, a sorbitol, and a glycerin derivative.

5. The dip molding process of claim 1, wherein the amino acid is at least one of: an L-glutamine and an L-asparagine.

6. The dip molding process of claim 1, wherein the vegetarian polishing agent is a plant wax.

7. The dip molding process of claim 1, wherein the pullulan polysaccharide is produced from at least one of corn starch or tapioca starch.

8. The dip molding process of claim 1, further comprising adding a coloring agent in a range from 0.001 percent to 2 percent based upon the weight of the allergen free solution.

9. The dip molding process of claim 8, wherein the coloring agent comprises at least one of azo-, quinophthalone-, triphenylmethane, xanthene- or indigoid dyes, iron oxides or hydroxides, titanium dioxide, natural dyes, and combinations thereof.

10. The dip molding process of claim 1, comprising dipping of the molding pins at least once.

11. The dip molding process of claim 1, further comprising filling each hard capsule shell with at least one active ingredient.

12. A hard capsule shell comprising:
a. 65 weight percent to 99 weight percent based on the total weight of an allergen free solution of pullulan polysaccharide with no more than 0.5 percent of the pullulan polysaccharide with a molecular weight greater than 810 kDa;
b. 0.5 weight percent to 15 weight percent based on the total weight of the allergen free solution of a neutrally charged hydrophilic amide derived from an amino acid;
c. 0.3 weight percent to 4.5 weight percent based on the total weight of the allergen free solution of a rheology modifier;
d. 0.3 weight percent to 4.5 weight percent based on the total weight of the allergen free solution of a plasticizer;
e. 0.01 weight percent to 0.6 weight percent based on the total weight of the allergen free solution of a chelating agent; and
f. a quantity sufficient (Q.S.) amount of water.

13. The hard shell capsule of claim 12, further comprising at least one encapsulated active ingredient.

14. The hard capsule shell of claim 13, wherein the at least one encapsulated active ingredient comprises a solid, a semi-solid, or a liquid form.

15. The hard capsule shell of claim 12, wherein the quantity sufficient (Q.S.) amount of water, as equilibrated with the relative humidity of the outside air, ranges from 2 percent to 20 percent by weight of the total weight of the hard capsule shell.

* * * * *